US008398694B2

(12) United States Patent
Forde et al.

(10) Patent No.: US 8,398,694 B2
(45) Date of Patent: *Mar. 19, 2013

(54) OVER-THE-WIRE INTERLOCK ATTACHMENT/DETACHMENT MECHANISM

(75) Inventors: Sean T. Forde, Watertown, MA (US); Steven W. Opolski, Carlisle, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1459 days.

This patent is subject to a terminal disclaimer.

(21) Appl. No.: 11/200,628

(22) Filed: Aug. 9, 2005

(65) Prior Publication Data

US 2006/0004434 A1    Jan. 5, 2006

Related U.S. Application Data

(62) Division of application No. 09/977,971, filed on Oct. 17, 2001, now Pat. No. 6,936,058.

(60) Provisional application No. 60/241,005, filed on Oct. 18, 2000.

(51) Int. Cl.
*A61F 2/06* (2006.01)

(52) U.S. Cl. ....... 623/1.11; 606/200; 606/108; 606/191; 606/198

(58) Field of Classification Search .................. 623/1.11; 606/108, 191, 195, 198, 200
See application file for complete search history.

(56) References Cited

U.S. PATENT DOCUMENTS

| 430,849 A | 6/1890 | Groth |
|---|---|---|
| 2,470,631 A | 8/1943 | McClellan |
| 2,890,900 A | 6/1955 | Williamson, Jr. et al. |
| 3,828,790 A | 8/1974 | Curtiss et al. |
| 3,837,690 A | 9/1974 | Fraser, Jr. et al. |
| 4,765,199 A | 8/1988 | Andersen et al. |
| 4,792,320 A | 12/1988 | Nickel |
| 4,969,879 A | 11/1990 | Lichte |
| 5,049,153 A | 9/1991 | Nakao et al. |
| 5,098,440 A | 3/1992 | Hillstead |
| 5,122,123 A | 6/1992 | Vaillancourt |
| 5,133,721 A | 7/1992 | Angulo |
| 5,171,233 A | 12/1992 | Amplatz et al. |
| 5,407,243 A | 4/1995 | Riemann |
| 5,464,408 A | 11/1995 | Duc |
| 5,511,559 A | 4/1996 | Vance |

(Continued)

FOREIGN PATENT DOCUMENTS

| DE | 709 732 | 8/1941 |
|---|---|---|
| DE | 1 179 889 | 7/1962 |

(Continued)

OTHER PUBLICATIONS

Supplemental European Search Report for PCT/US01/32184, mailed from the European Patent Office on Feb. 6, 2007.

(Continued)

*Primary Examiner* — Vy Q Bui
(74) *Attorney, Agent, or Firm* — DLA Piper LLP (US)

(57) ABSTRACT

The over-the-wire interlock attachment/detachment mechanism includes a cylindrical lock receiving section of a small diameter attached to an implantable medical device such as a blood clot filter, a stent, or a septal occluder. This cylindrical lock receiving section has a plurality of spaced, curved cutouts to receive both the guide fingers and contoured locking fingers formed on a cylindrical locking section. The locking fingers are angled outwardly from the cylindrical body of the cylindrical locking section, and are moved inwardly into engagement with the curved cutouts of the cylindrical lock receiving section by a sheath which slides over the cylindrical locking section or other suitable operator.

11 Claims, 3 Drawing Sheets

U.S. PATENT DOCUMENTS

| | | | |
|---|---|---|---|
| 5,601,595 A | 2/1997 | Smith | |
| 5,609,608 A | 3/1997 | Benett et al. | |
| 5,702,421 A | 12/1997 | Schneidt | |
| 5,800,457 A | 9/1998 | Gelbfish | |
| 5,810,864 A | 9/1998 | Schaller | |
| 5,820,612 A | 10/1998 | Berg | |
| 5,853,420 A | 12/1998 | Chevillon et al. | |
| 5,891,130 A | 4/1999 | Palermo et al. | |
| 5,910,144 A * | 6/1999 | Hayashi | 606/108 |
| 5,951,564 A | 9/1999 | Schroder et al. | |
| 5,984,378 A | 11/1999 | Ostrander et al. | |
| 6,059,825 A | 5/2000 | Hobbs et al. | |
| 6,099,534 A | 8/2000 | Bates et al. | |
| 6,099,549 A | 8/2000 | Bosma et al. | |
| 6,174,322 B1 | 1/2001 | Schneidt | |
| 6,187,016 B1 * | 2/2001 | Hedges et al. | 606/108 |
| 6,214,036 B1 * | 4/2001 | Letendre et al. | 623/1.11 |
| 6,238,415 B1 | 5/2001 | Sepetka et al. | |
| 6,270,525 B1 * | 8/2001 | Letendre et al. | 623/1.35 |
| 6,623,518 B2 | 9/2003 | Thompson et al. | |
| 2002/0120322 A1 | 8/2002 | Thompson et al. | |
| 2002/0120323 A1 | 8/2002 | Thompson et al. | |

FOREIGN PATENT DOCUMENTS

| | | |
|---|---|---|
| EP | 1000590 | 5/2000 |
| WO | 92/21400 | 12/1992 |
| WO | WO 02/32496 | 4/2002 |

OTHER PUBLICATIONS

International Search Report for PCT/US03/07911 dated Mar. 15, 2002.

* cited by examiner

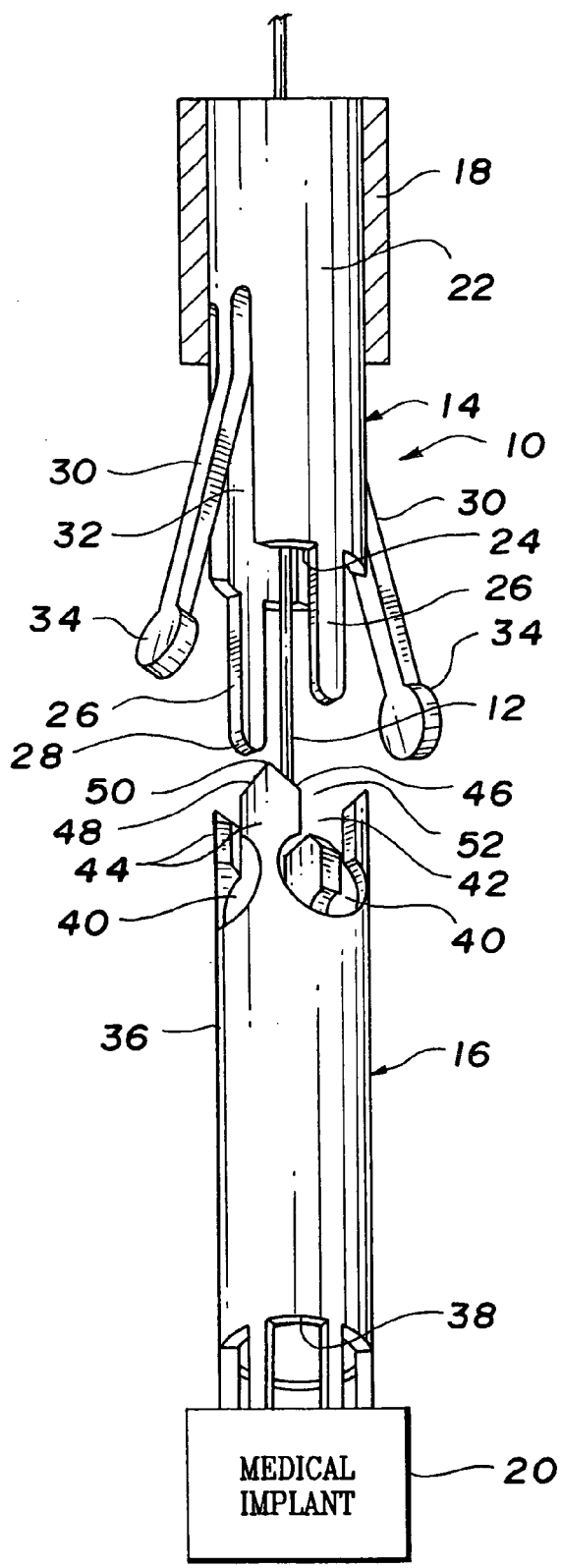
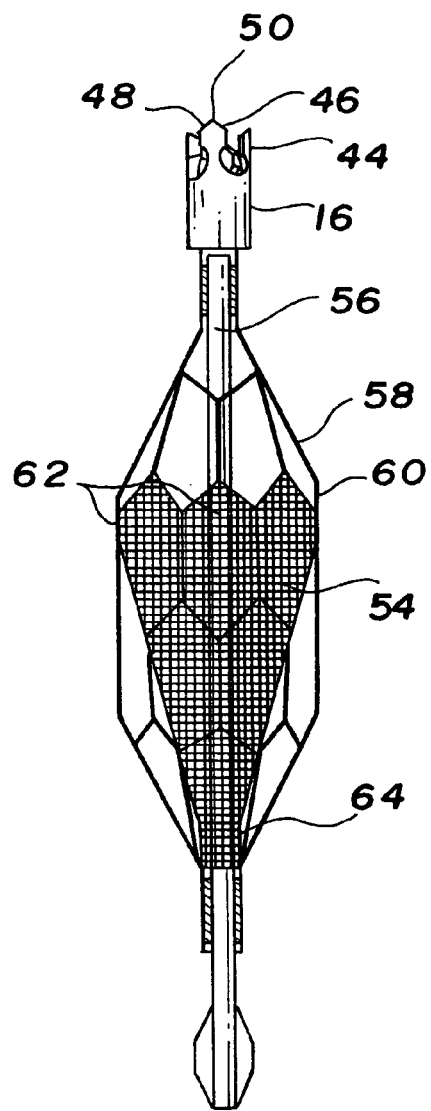
FIG. 1
FIG. 2

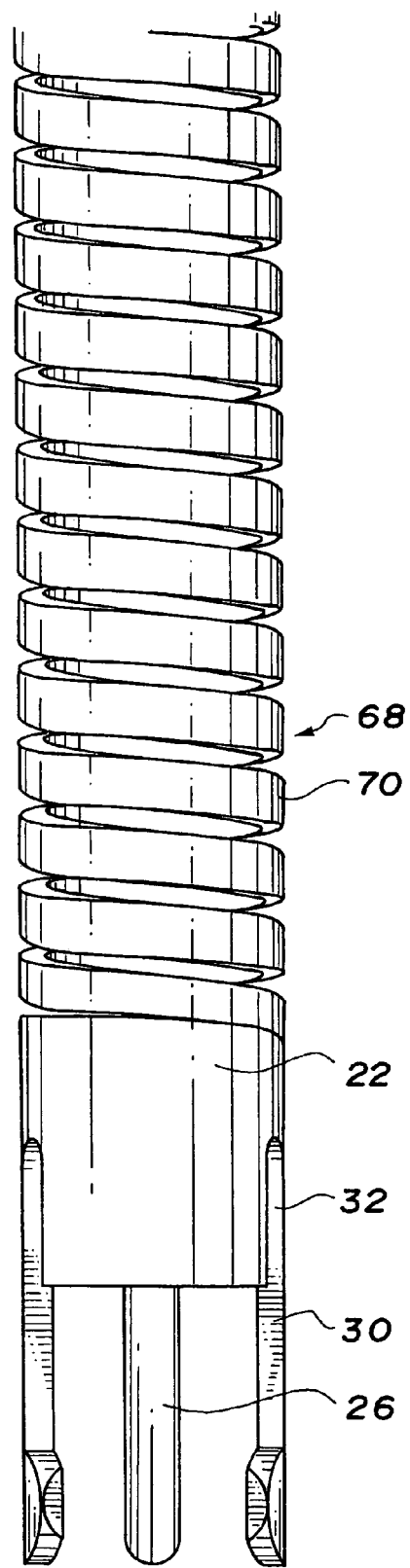
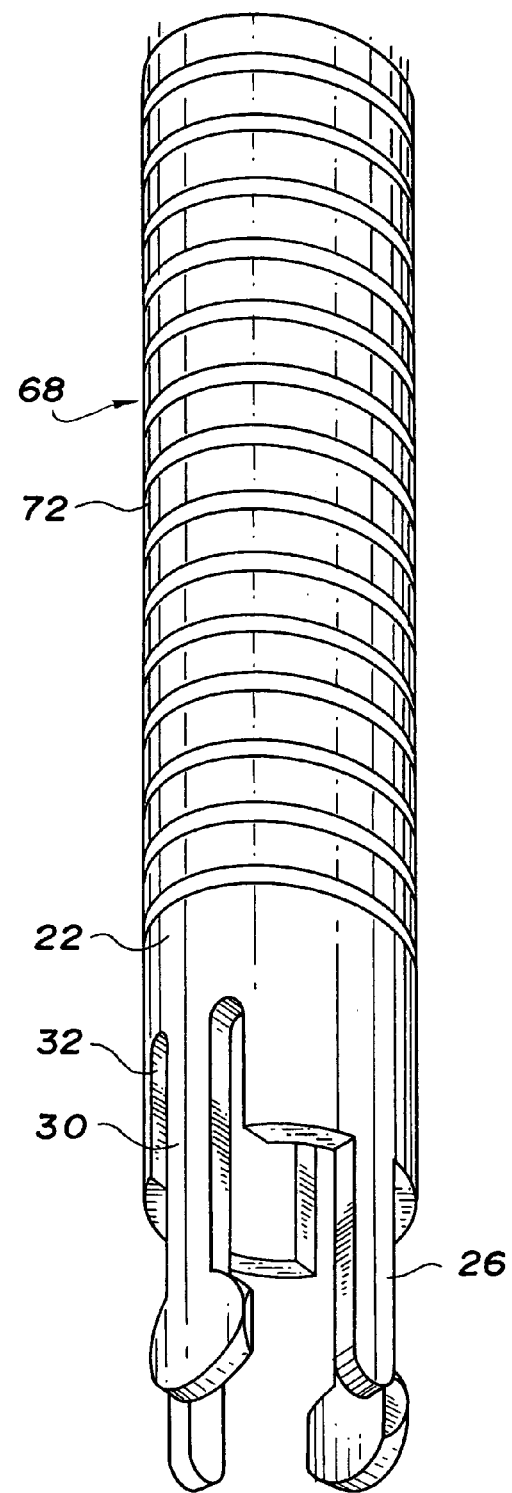
FIG. 5
FIG. 6

OVER-THE-WIRE INTERLOCK ATTACHMENT/DETACHMENT MECHANISM

This application is a divisional of U.S. patent application Ser. No. 09/977,971, filed Oct. 17, 2001, now U.S. Pat. No. 6,936,058, issued Aug. 30, 2005, and claims the benefit of provisional patent application Ser. No. 60/241,005, filed Oct. 18, 2000, the disclosures of which are incorporated herein by reference.

BACKGROUND OF THE INVENTION

In recent years, a number of medical devices have been designed which are adapted for compression into a small size to facilitate introduction into the heart or a vascular passageway and which are subsequently expandable. These devices, among others, include septal occluders, stents and free standing filters which expand and are held in position by engagement with the wall of an organ or vessel. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed to fit within the bore of a delivery catheter when exposed to a temperature below a predetermined transition temperature, but at temperatures at or above the transition temperature, the device expands and becomes relatively rigid.

Originally, these implantable medical devices were intended to permanently remain in place, but recently it has become advantageous to retrieve the previously implanted device.

The development of removable implantable medical devices such as septal occluders, stents and filters which expand and are held in position by engagement with the wall of an organ or vessel has led to the development of intra vascular snares to retrieve these foreign bodies, usually from the peripheral vessels of the cardiovascular system. Single loop snares, such as those shown by U.S. Pat. No. 3,828,790 to Curtiss et al. and U.S. Pat. No. 5,171,233 to Amplatz et al. are commonly used snares. The Amplatz snare consists of a super-elastic loop can be introduced through small lumen catheters without risk of deformation. The loop is formed at approximately 90° to a cable, and this allows for the user to advance the loop over a foreign body and ensnare it by closing the loop with a small catheter. The foreign body is removed from the vasculature by withdrawing the device into a guiding catheter or vascular sheath.

In an attempt to provide a snare with improved cross sectional vessel coverage, multi-loop snares such as those shown by U.S. Pat. No. 5,098,440 to Hillstead and U.S. Pat. No. 6,099,534 to Bates have been developed. These snares include loops which are joined only at their proximal ends to a shaft, and otherwise are not joined at any point between the shaft and the distal ends of the loops. This provides the advantage over single loop snares of enhanced cross sectional vessel coverage, and the free distal ends of the loops can be brought together to engage multiple surfaces of an intravascular medical device to be removed.

The problem with known snare recovery devices is that they are difficult to advance over a medical implant device and require skilled manipulation to retrieve an implanted device. Once the medical implant device is engaged by a recovery snare, there is no assurance that the device will not slip out of the snare during the recovery process.

It is particularly difficult to remove medical implants from the heart, such as septal occluders, with known snare recovery devices. Such snare recovery devices normally require appropriate sizing to the vasculature in order to facilitate successful ensnarement, and the geometry of multi loop snares is difficult to maintain during delivery. The relative position of the loops can change, both within a catheter or delivery tube and within a vessel, and the loops can actually become displaced or entangled during delivery.

SUMMARY OF THE INVENTION

A primary object of the present invention is to provide a novel and improved over-the-wire interlock attachment/detachment mechanism adapted to engage and positively lock on to an implanted medical device.

Another object of the present invention is to provide a novel and improved over-the-wire interlock attachment/detachment mechanism which automatically aligns to form an interlock attachment with an implanted medical device.

A further object to the present invention is to provide a novel and improved over-the-wire interlock attachment/detachment mechanism well adapted for use with over-the-wire implanted medical devices.

Yet another object of the present invention is to provide a novel and improved over-the-wire interlock attachment/detachment mechanism which includes a cylindrical locking section for engagement with a cylindrical lock receiving section connected to the medical implant.

A further object of the present invention is to provide a novel and improved over-the-wire interlock attachment/detachment mechanism which includes no overlapping components and which maintains a low profile configuration during passage through a vessel and/or catheter.

These and other objects of the present invention are achieved by providing a cylindrical lock receiving section of a small diameter attached to an implantable medical device such as a blood clot filter, a stent, or a septal occluder. This cylindrical lock receiving section has a plurality of spaced, curved cutouts to receive both the guide fingers and contoured locking fingers formed on a cylindrical locking section. The locking fingers are angled outwardly from the cylindrical body of the cylindrical locking section, and are moved inwardly into engagement with the curved cutouts of the cylindrical lock receiving section by a sheath which slides over the cylindrical locking section, or by another suitable operator which can be activated to move the fingers inwardly.

BRIEF DESCRIPTION OF THE DRAWINGS

FIG. 1 is a perspective view of the over-the-wire interlock attachment/detachment mechanism of the present invention with the control sheath shown in section;

FIG. 2 is a perspective view of an over-the-wire free standing filter with the cylindrical lock receiving section for the over-the-wire interlock attachment/detachment mechanism of FIG. 1;

FIG. 5 is a second embodiment of a locking section for the over-the-wire interlock attachment/detachment mechanism of the present invention; and FIG. 6 is a third embodiment of a locking section for the over-the-wire interlock attachment/detachment mechanism of the present invention.

DESCRIPTION OF THE PREFERRED EMBODIMENTS

Figure 3:
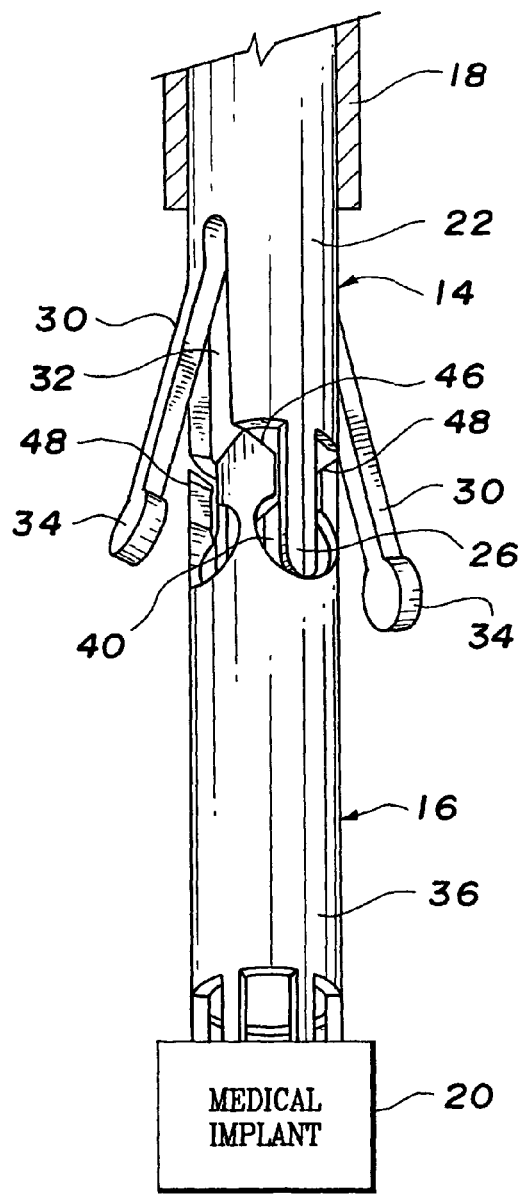
FIG. 3 is a perspective view of the partially engaged locking and lock receiving sections for the over-the-wire interlock attachment/detachment mechanism of FIG. 1.

Referring to FIG. 1, the over-the-wire interlock attachment/detachment mechanism of the present invention indicated generally at 10 is adapted for movement along a conventional guidewire 12 such as a 0.014" guidewire. The over-the-wire interlock attachment/detachment mechanism includes a male locking section 14, a female lock receiving section 16, and a tubular sheath 18 dimensioned to slide over the male and female sections. Preferably, the female section 16 is secured to an implantable medical device 20 such as a septal occluder, a filter or stent to be released in the heart or a blood vessel or other vessel of the human body or to be retrieved or repositioned within the heart or vessel.

The male locking section 14 includes a tubular body 22 which defines an open ended central chamber 24 through which the guidewire 12 passes. Projecting outwardly from the forward end of the tubular body 22 are one or more elongate guide fingers 26. These guide fingers are straight, elongate pins with arcutely shaped ends 28, and two such guide fingers are shown in FIG. 1 although more than two can be provided. The outer surface of each guide finger is preferably coextensive with the outer surface of the tubular body 22.

Also projecting outwardly from the forward end of the tubular body 22 are one or more flexible, elongate locking arms 30 which are substantially equal in width to the width of the guide fingers 26. Underlying each of the locking arms is a slot 32 formed in the tubular body to receive the locking arm. When unconfined, each locking arm is formed to angle outwardly beyond the outer surface of the tubular body 22.

A shaped locking member 34 is formed at the end of each locking arm. Preferably, this locking member, which extends laterally from at least one side of the locking arm, is circular in shape, but other shapes which extend laterally from the locking arm including but not limited to an ellipse, a "T", a rectangle, a square, a hook, a triangle or an "L" can be used. A circular locking member facilitates engagement with the lock receiving section 16. The guide fingers and locking arms are equally spaced around the tubular body 22. They are preferably equal in number, and although two of each are shown, more can be used.

The female lock receiving section 16 includes a tubular body 36 which defines an open ended central chamber 38 for receiving the guidewire 12. The tubular body 36 is substantially equal in diameter to the tubular body 22 so that the two are coextensive when the male locking section is engaged with the female lock receiving section.

The female lock receiving section includes a plurality of shaped locking cutouts 40 which are shaped to conform to and receive the shaped locking members 34. The number of shaped locking cutouts 40 is equal to the number of guide fingers 26 and locking arms 30. Extending into each of the shaped locking cutouts 40 is a straight, open ended, cutout entry section 42 which is formed to receive either a guide finger 26 or a locking arm 30.

The shaped locking cutouts 40 and open ended entry cutout sections 42 are equally spaced around the tubular body 36 to conform to the spacing of the guide fingers 26 and locking arms 30. Outwardly projecting spacer sections 44 extend outwardly between adjacent shaped cutouts and open ended entry cutout sections and each terminate in inclined outer end surfaces 46 and 48 which form an apex 50. Each inclined outer surface angles downwardly toward an open ended entry cutout section 42 and the inclined outer end surface 46 of a spacer section 44 forms with the inclined outer end surface 48 of an adjacent spacer section an enlarged outwardly tapered opening 52 for each open ended cutout section.

The female lock receiving section 16 is secured to one end of a medical implant 20, which can be an over the wire device such as a septal occluder. For purpose of illustration, the female lock receiving section is shown with the over-the-wire free standing filter 54. The free standing filter 54 has a filter body with an elongate guidewire receiving member 56 extending centrally therethrough to define an open ended channel configured to receive a plurality of different sized guidewires. An expandable and contractible frame 58 surrounds the elongate guidewire receiving member and is connected at a proximal end to the elongate guidewire receiving member. A porous embolic capturing unit 60 has an open end 62 connected to the frame and a closed end 64 connected to the elongate guidewire receiving member which extends through the porous embolic capturing unit.

Figure 4:
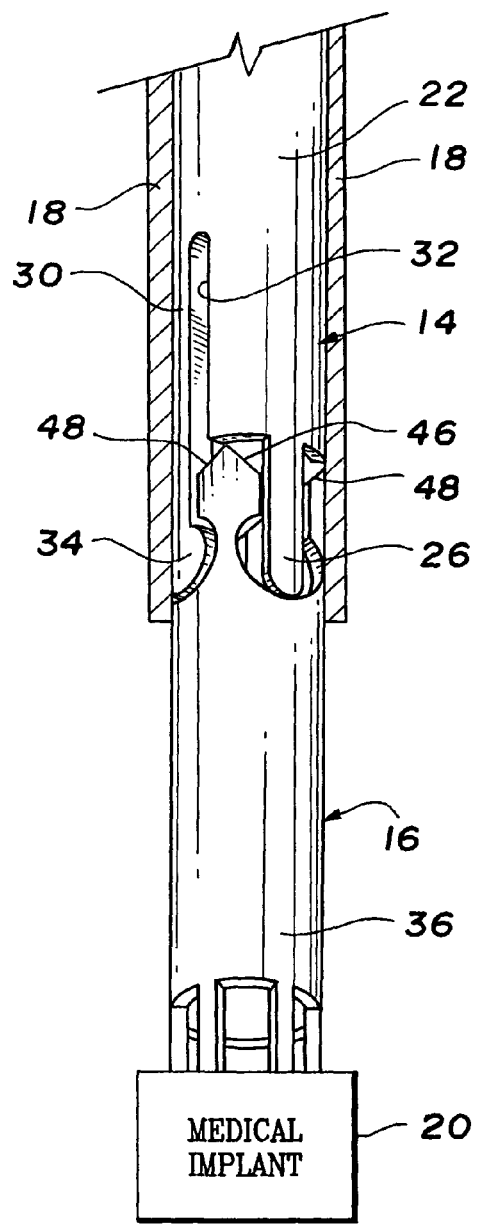
FIG. 4 is a perspective view of the engaged locking and lock receiving sections for the over-the-wire interlock attachment/detachment mechanism of FIG. 1.

FIGS. 1, 3 and 4 disclose the manner in which the over-the-wire interlock attachment/detachment mechanism 10 is operable to positively engage and remove a medical implant 20 from a body organ or vessel. The male locking section 14 is enclosed within the sheath 18 so that the locking arms 30 are forced into the slots 32 and do not project outwardly beyond the periphery of the male locking section. In this configuration, the male locking section is passed along the wire 12 until it is positioned in close proximity to the female lock receiving section 16. At this point, the sheath 18 is drawn back to permit the locking arms 30 to angle outwardly from the male locking section 14. The male locking section is then moved toward the female lock receiving section 16 until the guide fingers 26 engage the outer end surface 46 or 48 of a spacer section 44. As the male locking section continues to move toward the female lock receiving section, each guide finger will be guided by an inclined outer end surface 46 or 48 into an open ended cutout entry section 42 which then guides the guide finger into the associated shaped cutout 40. The over-the-wire interlock attachment/detachment mechanism is now in the configuration illustrated in FIG. 3. It will be noted that when the guide fingers move into the open ended cutout entry sections 42, they position the locking arms 30 and the locking members 34 above and in alignment with open ended cutout sections 42 and their associated shaped cutouts 40. Now, shown in FIG. 4, the tubular sheath 18 is moved forwardly over the tubular bodies 22 and 36 to force the locking members 34 into the shaped cutouts 40 and positively engage the male locking section 14 with the female lock receiving section 16.

Once a positive engagement has been established between the male locking section and female lock receiving section, the over-the-wire interlock attachment/detachment mechanism can be drawn back over the wire 12 to remove-the medical implant 20. Because of the positive locking engagement, forces present on the medical implant as it is withdrawn will not result in detachment from the over-the-wire interlock attachment/detachment mechanism. This is very important for medical implants such as the removable filter 54 where hooks 58 must be withdrawn from the wall of the vessel.

It is often difficult to accurately position a medical implant within a vessel without disconnecting or misaligning the implant relative to the positioning device. This problem is rectified by the over-the-wire interlock attachment/detachment mechanism 10. The medical implant 20 with an attached female lock receiving section 16 is positively locked to the male locking section 14 in the manner shown by FIG. 4 before it is moved over the wire 12 into position within a body vessel. The positive locking action between the male locking section and female lock receiving section facilitates accurate positioning of the medical implant within a vessel without misorientation or the likelihood of a disconnect. Once the implant device is positioned, the sheath 18 can be moved back as shown in FIG. 3 allowing the locking arms 30 to spring outwardly to disengage the locking members 34 from the shaped cutouts 40. Now the male locking section 14 can be drawn back over the wire 12 away from the female lock receiving section 16.

The sheath 18 may be replaced by other operating mechanisms capable of moving the locking arms 30 into the slots 32. For example, elongate tethers attached to the ends of the locking arms which extend back through the central chamber 24 might perform this function.

The male locking section 14 can be modified as shown in FIGS. 5 and 6 to provide a flexible end section 68 adjacent to the elongate guide fingers 26 and elongate locking arms 30. By providing a flexible section 68 in the body 22 proximal to the guide fingers and locking arms, it becomes easier to align the guide fingers, locking arms and locking members 34 with the cutouts in the female lock receiving section 16. The flexible section 68 can be formed in a variety of ways. For example, a spring section can be welded or bonded to the body 22 between the main portion of the body and the guide fingers and locking arms to form the flexible section 68. Ideally, as shown in FIG. 5, the body 22 is formed with a unitary spring section 68 by cutting the body in a spiral to create a helical spring 70. This can be done with a laser which can also be used to shape the guide fingers, locking arms and locking members in the tubular body Alternatively, as shown in FIG. 6, a flexible, tubular polymer section 72 can be formed between the main portion of the body 22 and the guide fingers and locking arms to provide the flexible section 68.

We claim:

1. A medical implant delivery system comprising:
   a catheter defining a shaft having a longitudinal lumen extending from a proximal end to a distal end, the distal end comprising a male locking section having a male locking arm extendable from a wall of the shaft and a lumen for a guidewire to pass therethrough, wherein said male locking arm, when unrestrained, releases laterally and angularly outward; and
   a sheath reversibly slidable over the male locking section thereby allowing the male locking arm to repeatedly transition reversibly between a first state and a second state, wherein the sheath restrains the male locking arm in the first state when slid over the male locking section and releases the male locking arm into the second state when slid away from the male locking section, wherein the transition causes the male locking arm to engage and disengage a female locking section disposed distal to the male locking, wherein the female locking section is attached to an implant.

2. The delivery system of claim 1 wherein the male locking arm extends, in the first state, substantially parallel to a longitudinal axis of the distal end of the shaft.

3. The delivery system of claim 1 wherein the male locking arm extends, in the second state, laterally and angularly outward from a longitudinal axis of the distal end of the shaft.

4. The delivery system of claim 1 wherein the male locking arm comprises an enlargement at its free end.

5. The delivery system of claim 4 wherein the enlargement is substantially circular.

6. The delivery system of claim 1 wherein the male locking section comprises multiple locking arms spaced substantially equidistant around the longitudinal lumen at the distal end.

7. The delivery system of claim 1, wherein the implant is implant attached to the female locking section through a cutout section in the implant that receives a female locking arm extending from the female locking section.

8. The delivery system of claim 7 wherein the implant is selected from the group consisting of an occluder, a filter, and a stent.

9. The delivery system of claim 7 wherein the implant and the female locking section are axially aligned when the female locking arm is received in the cutout section.

10. The delivery system of claim 1 further comprising a guidewire.

11. The delivery system of claim 1 further comprising a flexible section.

* * * * *